United States Patent [19]

Marsham

[11] 4,096,337

[45] Jun. 20, 1978

[54] PROSTANE DERIVATIVES

[75] Inventor: Peter Robert Marsham, Macclesfield, England

[73] Assignee: Imperial Chemical Industries Limited, London, England

[21] Appl. No.: 691,297

[22] Filed: Jun. 1, 1976

[30] Foreign Application Priority Data

Jun. 13, 1975 United Kingdom ............... 25378/75

[51] Int. Cl.² ............................................. C07C 69/76
[52] U.S. Cl. ..................................... 424/308; 424/341; 260/343.3 P; 260/345.7 P; 260/514 D; 260/520 C; 260/520 R; 260/590 C; 260/619 D; 560/21; 560/53; 560/55; 560/100; 560/59; 560/102; 560/121; 560/56; 424/343; 424/309; 424/317; 424/331; 542/426; 568/705; 568/807; 568/808

[58] Field of Search ...................... 260/473 R, 473 F

[56] References Cited

FOREIGN PATENT DOCUMENTS 2,510,818  3/1974  Germany ............................. 260/473

Primary Examiner—Paul J. Killos
Attorney, Agent, or Firm—Cushman, Darby & Cushman

[57] ABSTRACT

The disclosure relates to novel 15-(3-aryl- or 3-aralkyl-cyclobutyl, -cyclopentyl and -cyclohexyl)-ω-pentanor prostaglandin analogues, for example 9α,11α,15α-trihydroxy-15-(trans-3-phenylcyclobutyl)-16,17,18,19,20-pentanor-5-cis,13-trans-prostadienoic acid, to pharmaceutical or veterinary compositions containing such a compound, and to a method of inducing luteolysis in animals by orally administering such a compound.

9 Claims, No Drawings

PROSTANE DERIVATIVES

This invention relates to prostane derivatives, and in particular it relates to prostane derivatives which possess a high level of luteolytic activity. The new derivatives are therefore advantageous when used as contraceptives, for control of the oestrous cycle in animals, for the induction of labour or for the termination of early pregnancy. The compounds may also be useful as hypotensives, for the relief of bronchospasm, or as inhibitors of gastric secretion or blook platelet aggregation.

According to the invention, there is provided a prostane derivative of the formula:-

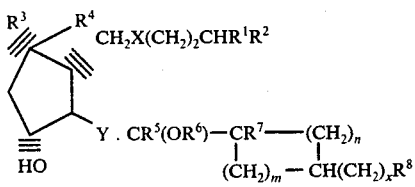

I wherein $R^1$ is a carboxy or hydroxymethyl radical, a $C_{2-5}$ alkoxycarbonyl radical or a $C_{2-5}$ alkoxymethyl radical, $R_2$, $R^5$, $R^6$ and $R^7$ are each a hydrogen atom or a $C_{1-4}$ alkyl radical, either $R^3$ is a hydroxy radical and $R^4$ is a hydrogen atom or $R^3$ and $R^4$ together form an oxo radical, $R^8$ is a phenyl or naphthyl radical, optionally bearing one or more substituents selected from haolgen atoms, nitro and phenyl radicals, and $C_{1-4}$ alkyl, halogenoalkyl and alkoxy radicals, X is an ethylene or vinylene radical, Y is an ethylene or transvinylene radical, $m$ and $n$, which may be the same or different, are each 1 or 2, and $x$ is 0 or 1, and for those compounds wherein $R^1$ is a carboxy radical, the pharmaceutically or veterinarily acceptable base addition salts thereof.

Suitable values for $R^1$ when it is a $C_{2-5}$ alkoxycarbonyl or alkoxymethyl radical are methoxycarbonyl, ethoxycarbonyl, butoxycarbonyl, methoxymethyl, ethoxymethyl and butoxymethyl radicals. A preferred value for $R^1$ is a carboxy, hydroxymethyl or methoxycarbonyl radical.

A suitable value for $R^2$, $R^5$, $R^6$ or $R^7$, when any one or more of them is a $C_{1-4}$ alkyl radical, is a methyl, ethyl, propyl or butyl radical, particularly a methyl radical.

Suitable halogen substituents in $R^8$ are, for example, chorine, fluorine or bromine atoms, especially chlorine and fluorine atoms, and suitable $C_{1-4}$ alkyl, halogenolkyl and alkoxy radicals are, for example, methyl, ethyl, propyl, butyl, trifluoromethyl, methoxy, ethoxy, propoxy and butoxy radicals, particularly methyl, trifluoromethyl and methoxy radicals. Preferred radicals $R^8$ bear only one such substituent.

A preferred value for X when it is a vinylene radical is, for example, a cis-vinylene radical. Examples of base addition salts are the ammonium, alkylammonium containing 1 to 4 $C_{1-6}$ alkyl radicals, alkanolammonium containing 1 to 3 2-hydroxyethyl radicals and alkali metal salts, for example the triethylammonium, ethanolammonium, diethanolammonium, sodium and potassium salts.

It will be observed that the compounds of the formula I contain at least 6 asymmetric carbon atoms, namely carbon atoms 8, 11, 12, 15 and 16 of the prostane nucleus, and the carbon atom to which the group —$(CH_2)_x R^8$ is attached, and that carbon atoms 2 and 9 may also be asymmetrically substituted, so that is is clear that, even though the relative configurations of carbon atoms 8, 11 and 12 are fixed, the compounds of the invention may exist in a variety of racemic and optically active forms. It is to be understood that the useful properties of a racemate of the invention may be present to different extents in the optical isomers, and that this invention relates to any racemic, or optically active, form which shows the above useful properties, it being a matter of common general knowledge how the optically active forms may be obtained, and to determine their respective biological properties.

A preferred group of compounds of the invention compriese those compounds wherein $R^1$ is a carboxy, hydroxymethyl or methoxycarbonyl radical, $R^2$, $R^5$ and $R^6$ are hydrogen atoms, $R^7$ is a hydrogen atom or a methyl radical, $R^3$ is a hydroxy radical, $R^4$ is a hydrogen atom, X is a cis-vinylene radical, Y is a trans-vinylene radical, X is 0, $m$ and $n$ are each 1, and $R^8$ is a phenyl radical, optionally substituted by a chlorine or fluorine atom or a methyl or trifluoromethyl radical, or unsubstituted naphthyl radical, particularly a phenyl, 3-trifluoromethylphenyl, 3-tolyl, 4-fluorophenyl, 4-chlorophenyl or 1-napthyl radical.

A particular preferred compound of the invention is 9α11α, 15α-trihydroxy-15-(trans-3-phenyl-cyclobutyl)-16, 17, 18, 19, 20-pentanor-5-cis,13-trans-prostadienoic acid.

The prostane derivatives of the invention may be manufactured by methods known in themselves for the manufacture of chemically analogous compounds. Thus, the following processes are provided as further features of the invention, wherein $R^1$, $R^2$, $R^3$, $R^4$, $R^5$, $R^6$, $R^7$, $R^8$, X, Y, $m$, $n$ and $x$ have the meanings stated above, unless otherwise specified:-

(a) for those compounds wherein $R^1$ is a carboxy or alkoxycarbonyl radical, the hydrolysis under acidic conditions of a compound of the formula:

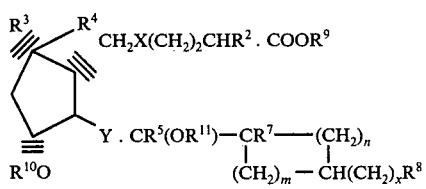

II wherein $R^9$ is a hydrogen atom or a $C_{1-4}$ alkyl radical, $R^{10}$ is a tetrahydropyran-2-yl radical, and $R^{11}$ is a $C_{1-4}$ alkyl radical or a tetrahydropyran-2-yl radical, for example with acetic acid, or with toluene-p-sulphonic acid in a $C_{1-4}$ alkanol; or (b) for those compounds wherein $R^1$ is an alkoxycarbonyl radical, the reaction of the arboxylic acid of the formula I, wherein $R^1$ is a carboxy radical, with a $C_{1-4}$ diazoalkane, or fo a salt thereof, for example a sodium or silver salt, with a $C_{1-4}$ alkyl halide, for example an alkyl bromide or alkyl iodide; or (c) for those compounds wherein $R^1$ is a hydroxymethyl radical, $R^3$ is a hydroxy radical and $R^4$ is a hydrogen atom, the reduction of a compound of the formula I wherein $R^1$ is an alkoxycarbonyl radical, for example with a complex metal hydride such as lithium aluminum hydride; or (d) for those compounds wherein $R^3$ is a hydroxy radical and $R^4$ is a hydrogen atom, the basic hydrolsis of a compound of the formula:

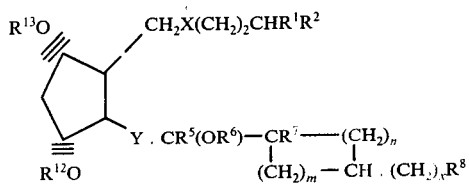

wherein $R^{12}$ is a hydrogen atom or an aroyl radical of up to 15 carbon atoms, for example a 4-phenylbenzoyl radical, and $R^{13}$ is an aroyl radical of up to 15 carbon atoms, for example a 4-phenylbenzoyl radical, with, for example, an alkali metal hydroxide such as potassium hydroxide or an alkali metal carbonate such as potassium carbonate in an inert solvent; or (e) for those compounds wherein $R^1$ is an alkoxycarbonyl or alkoxymethyl radical and $R^6$ is an alkyl radical, the reaction of a corresponding compound of the formula I wherein $R^6$ is hydrogen atom with an alkyl halide, for example an alkyl bromide, in the presence of approximately one equivalent of a strong base, such as sodium hydride; or (f) for those compounds wherein $R^3$ is a hydroxy radical and $R^4$ is a hydrogen atom, the reduction of a corresponding compound of the formula I wherein $R^3$ and $R^4$ together form an oxo radical, for example with a complex metal hydride such as sodium bobohydride.

A starting material of the formula II wherein $R^9$ is a hydrogen atom, $R^2$, $R^4$, $R^5$, $R^7$ are each a hydrogen atom, $R^3$ is a hydroxy radical, X is a cis-vinylene radical, Y is a trans-vinylene radical, and $R^{11}$ is tetrahydropyran-2-yl radical, may be prepared by reacting 4β-formyl-2,3,3aβ,6aβ-tetrahydro-2-oxo-5α-(4-phenylbenzoylozy)cyclopenteno[b]furan (IV) with a phosphonate reagent of the formula $(MeO)_2PO.CH_2COR$, wherein R is a group of the formula

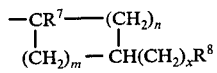

in the presence of a strong base, to give an enone V. The enone V is reduced, for example with aluminium tri-isopropoxide or di-isobornyloxy aluminium isopropoxide to an enol VI, which is hydrolysed, for example with potassium carbonate in methanol, to remove the protecting 4-phenylbenzoyl radical, giving a diol VII. The diol is protected as the bis(teytrahydropyranyl ether) VIII, by reaction with dihydropyran, and the lactone ring is reduced to a lactol IX using, for example di-isobutyl aluminium hydride. The lactol IX is then treated with a (4-carboxybutyl)triphenylphosphonium bromide in the presence of a strong base, to give a starting material of the formula II. The conditions for this last reaction may, of course, be chosen so as to produce predominantly either the 5-cis or the 5-trans compound, in known manner.

The phosphonate reagent $(MeO)_2PO.CH_2COR$ wherein R is a 3-phenylcyclobutyl radical may be prepared from the known 3-phenylcyclobutane carboxylic acid by conversion to the methyl ester, which in turn is treated with dimethyl methylphosphonate in the presence of a strong base such as butyl-lithium. Analogous phosphonate reagents required for the manufacture of other starting materials II may be prepared in an exactly similar way.

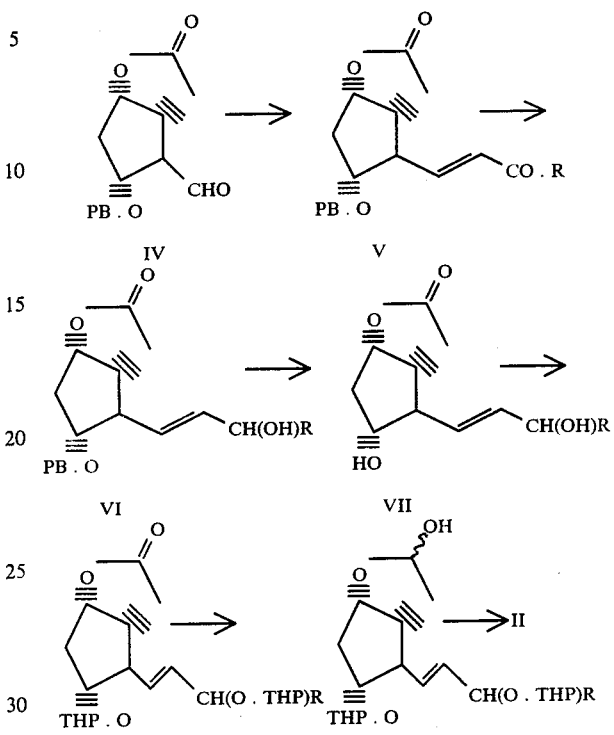

PB = 4-phenylbenzoyl
THP = tetrahydropyran-2-yl

A corresponding starting material of the formula II wherein X is an ethylene radical may be obtained by selective hydrogenation of a corresponding compound of the formula II wherein X is a cis-vinylene radical.

A corresponding starting material of the formula II wherein Y is an ethylene radical may be prepared by hydrogenation of a corresponding enone intermediate V to give a saturated ketone, which is then used in the above-described reaction sequence in place of the enone V.

A corresponding starting material of the formula II wherein $R^{11}$ is an alkyl radical may be prepared by alkylating an enol VI to an alkyl ether, which is then used in place of the enol VI in the above-described reaction sequence.

A corresponding starting material of the formula Ii wherein $R^3$ and $R^4$ together form an oxo radical may be obtained by the oxidation of the corresponding compound of the formula II wherein $R^3$ is a hydroxy radical and $R^4$ is a hydrogen atom, for example with Jones' reagent.

A compound of the formula III which may be used as a starting material in the process of the invention may be manufactured from an appropriate aldehyde X by reaction thereof with a phosphonate of the formula $(MeO)_2PO.CH_2COR$ as defined above, in the presence of a base, to give an enone XI, which is reduced, for example with aluminium tri-isopropoxide or di-isobornyloxy aluminium isopropoxide to give a starting material of the formula III wherein Y is a trans-vinylene radical and $R^6$ is a hydrogen atom.

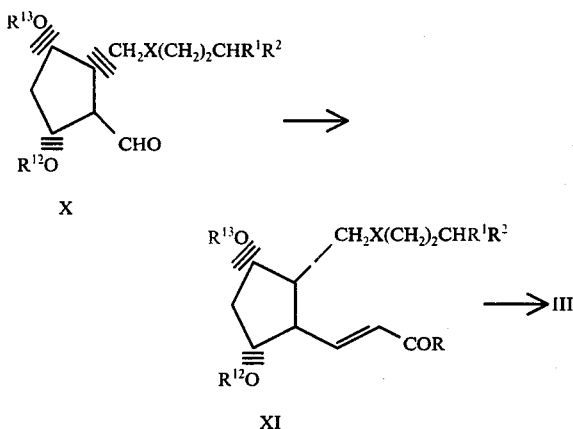

A corresponding starting material of the formula III wherein Y is an ethylene radical may be obtained by reducing an enone X with a complex metal hydride, for example sodium borohydride.

It is, of course, to be understood that an optically active compound of the invention may be obtained either by resolving a corresponding racemate, or by carrying out the above described reaction sequences starting from an optically active intermediate, for example an optically active aldehyde IV.

As stated above, the compounds of the invention possess luteolytic properties, and in particular they are more active as luteolytic agents and less active as smooth muscle stimulants than the naturally occurring prostaglandins. Thus, for example 9α,11α,15α-trihydroxy-15-(trans-3-phenylcyclobutyl)-16,17,18,19,20-pentanor-5-cis, 13-transprostadienoic acid is approximately 100 times as active as natural prostaglandin $F_2\alpha$ as a luteolytic agent in hamsters (subcutaneous dosing). No indications of toxicity have been noted, at the optimum lutolytic doses, in experimental animals.

When a compound of the invention is to be used for the induction of labour, it is used in the same way as it is known to use the naturally occurring prostaglandin $E_2$, that is by administering a sterile, substantially aqueous solution containing from 0.01 to 10μ./ml., preferably 0.01 to 1μ./ml. of the compound, by intravenous infusion, or by transcervical extra-amniotic or intraamniotic infusion until labour commences.

Also, for this purpose, the compounds of the invention may be used in combination, or concurrently, with a uterine stimulant, for example oxytocin, in the same way that it is known to use prostaglandin $F_2\alpha$ in combination, or concurrently with oxytocin for the induction of labour.

When a compound of the invention is to be used for the control of the oestrus cycle in animals, it may be used in the same way as it is known to use the luteolytic prostaglandin analogues cloprostenol and fluprostenol. It may also be used in combination, or concurrently, with a gonadotrophin, for example PMSG (pregant mare serum gonadotrophin) or HCG (human chorionic gonadotrophin) to hasten the one set of the next cycle.

Thus, according to a further feature of the invention there is provided a pharmaceutical or veterinary composition comprising a prostane derivative of the invention, together with a pharmaceutically or veterinarily acceptable diluent or carrier.

The compositions may be in a form suitable for oral administration, for example tablets or capsules, in a form suitable for inhalation, for example an aerosol or a solution suitable for spraying, in a form suitable for parenteral administration, for example sterile injectable aqueous or oily solutions or suspensions, or in the form of a suppository or pessary, suitable for anal or vaginal use. As stated above, when the compound of the invention is to be used for the induction of labour in childbirth, a preferred composition of the invention is a sterile, substantially aqueous, injectable solution containing from 10 to 250μg./ml., preferably 50 to 100 μg./ml. of the prostane derivative.

The compositions of the invention may be prepared by conventional means, and may incorporate conventional excipients.

The invention is illustrated, but not limited, by the following Examples. $R_F$ values refer to thin layer chromatography on silica gel plates supplied commercially by Merck of Darmstadt, and the spots were detected either by fluorescence, or by spraying the plates with a solution of ceric ammonium nitrate in sulphuric acid. 'Kieselgel 60' (trade mark) used for dry column chromatography was supplied commercially by Merck of Darmstadt. Before use it was deactivated by the adsorption of 10% w/w of water and then equilibrated by the adsorption of 10% v/w of the eluting solvent. Mass spectrum data for F-series compounds refer to the per-(trimethylsilyl) derivatives, that is, normally, tetra(trimethylsilyl) derivatives of compounds wherein $R^1$ is carboxy or hydroxymethyl, and tris(trimethylsilyl) derivatives of compounds wherein $R^1$ is an alkoxycarbonyl radical. Mass spectrum data for E-series compounds refer normally to the tris(trimethylsilyl)-9-methoxime derivatives.

EXAMPLE 1

A solution of 9α-hydroxy-15-(trans-3-phenyl cyclobutyl)-11α,15-bis-(tetrahydropyran-2-yloxy)-16,17,18,19,20-pentanor-5-cis,13-trans-prostadienoic acid (80mg.) in a mixture of water (2ml.), glacial acetic acid (1ml.) and tetrahydrofuran (1.5ml.) was stirred at 55° C. for 4 hours. The solvents were evaporated under reduced pressure with the aid of added toluene. The residue was chromatographed on thin layer silica gel plates, using a mixture of 5% acetic acid in ethyl acetate as a developing solvent, to give the separated C-15 epimers of 9α,11α,15-trihydroxy-15-(trans-3-phenylcyclobutyl)-16,17,18,19,20-pentanor-5-cis,13-trans-prostadienoic acid, $R_F$ = 0.45 and 0.30. The n.m.r. spectrum of each epimer in hexadeuterioacetone showed the following characteristic signals (δ values):-

7.1–7.3, 5H, multiplet, aromatic protons
5.2–5.8, 4H, multiplet, olefinic protons
3.8–4.3, 3H, multiplet, 3 = >C$\underline{H}$(OH)
3.4–3.8, 1H, multiplet, PhC$\underline{H}$<

The mass spectrum of the tetra-(trimethylsilyl) derivative of the more polar epimer had M⊕= 702.3991.
(Calculated for $C_{37}H_{66}O_5Si_4$ = 702.3988)

The bis(tetrahydropyranyl ether) used as the starting material was prepared as follows:-

A mixture of the cis and trans isomers of 3-phenylcyclobutane carboxylic acid (6.8g.) in methanol (100ml.) and concentrated suphuric acid (0.5ml.) was refluxed overnight. The solution was concentrated to about 15ml., water was added and the mixture was extracted with ethyl acetate. The ethyl acetate extracts were combined and dried over anhydrous magnesium sulphate, the solvent was evaporated and the residue was distilled, to give methyl 3-phenylcyclobutanecarboxylate as a mixture of cis- and trans-isomers, b.p. 100°–120° C./0.2 mm. Hg.

n-Butyl-lithium (16.0ml. of a 1.43M solution in hexane) was added dropwise to a stirred solution of dimethyl methylphosphonate (2.86g.) in dry tetrahydrofuran (25ml.) at −78° C. in an atmosphere of argon. After 10 minutes, a solution of the methyl 3-phenylcyclobutanecarboxylate mixture (2.18g.) in dry tetrahydrofuran (25ml.) was added, and stirred at −78° C. for 2 hours. The reaction mixture was then neutralized by the addition of glacial acetic acid, warmed to room temperature and the tetrahydrofuran was evaporated under reduced pressure. The residue was partitioned between ethyl acetate and water. The ethyl acetate extract was dried over magnesium sulphate and evaporated under reduced pressure, to give dimethyl 2-oxo-2-(3-phenylcyclobutyl)-ethylphosphonate, as a mixture of cis and trans isomers. The n.m.r. spectrum in deuteriochloroform showed the following characteristic features (δ values):-

7.20, 5H, singlet, aromatic protons
3.75, 6H, doublet, $(CH_3O)_2PO-$ 3.10 ⎫
3.05 ⎬ 2H, two doublets, $-CO.CH_2.PO<$ of cis and trans isomers.

A solution of this phosphonate mixture (2.82g.) and 4β-formyl-2,3,3aβ,6aβ-tetrahydro-2-oxo-5α-(4-phenylbenzoyloxy)-cyclopenteno[b]furan (2.30g.) in 9:1 toluene:t-butanol (50ml.) was stirred overnight with 1N aqueous sodium hydroxide solution (7.3ml.) in an argon atmosphere. The reaction mixture was neutralized with glacial acetic acid, water was added and the mixture was extracted with ethyl acetate. The ethyl acetate extracts were dried over magnesium sulphate, and the solvent was evaporated. The crude product was purified by dry column chromatography on "Kieselgel 60". Elution with toluene:ethyl acetate (4:1 by volume) yielded 2,3,3aβ,6aβ-tetrahydro-2-oxo-4β-[3-oxo-3-(3-phenylcyclobutyl)prop-1-trans-enyl]-5α-(4-phenylbenzoyloxy)cyclopentenc[b]-furan as separated cis and trans isomers about the cyclobutane ring, $R_F = 0.40$ and 0.48 (silica gel, 35% v/v ethyl acetate in toluene). The n.m.r. spectrum of each isomer in deuteriochloroform showed the following characteristic signals (δ values):-

3.1–3.6, 2H, multiplet, protons at C-1 and C-3 of cyclobutane ring,
5.1–5.2 and
5.2–5.5 2H, multiplets, 2 × > $CH.O.CO-$
6.25, 1H, doublet, olefinic proton To the trans-isomer of the above unsaturated ketone (340mg.) was added a solution of di-isobornyloxyaluminum isopropoxide (2.1 mmoles) in toluene. After 30 minutes at room temperature, saturated sodium hydrogen tartrate solution was added, and the mixture was stirred for 10 minutes. Ethyl acetate was added, and the organic phase was separated and dried, and the solvent was evaporated to yield a mixture of epimeric enols, which was contaminated with isoborneol, which was removed by trituration of the crude material with pentane. $R_F = 0.21$ and 0.15 (silica gel, 30% v/v ethyl acetate in toluene).

To a solution of the epimeric enol mixture (429 mg.) in dry methanol (25 ml.) and methylene chloride (5ml.) was added powdered anhydrous potassium carbonate (345 mg.). The solution was stirred for 3 hours in an argon atmosphere, the solution was neutralized with 1N hydrochloric acid, and evaporated almost to dryness. The residue was partitioned between brine and ethyl acetate, the ethyl acetate layer was separated, and the solent was evaporated to yield an epimeric mixture of 2,3,3aβ,6aβ-tetrahydro-5α-hydroxy-4β-[3-hydroxy-3-(3-trans-phenylcyclobutyl)prop-1-trans-enyl]-2-oxocyclopenteno[b]furan. This was dissolved in dry methylene chloride and treated with redistilled dihydropyran (0.64 ml.) and a 1% w/v solution of toluene-p-sulphonic acid in tetrahydrofuran (0.2 ml.). After 10 minutes, pyridine (3 drops) was added, followed by ethyl acetate (40 ml.). The solution was washed successively with saturated sodium bicarbonate solution and saturated brine, and was then dried. Evaporation of the solvents gave a mixture of epimeric bis-tetrahydropyranyl ethers, 2,3,3aβ,6aβ-tetrahydro-4β-[3-(3-trans-phenylcyclobutyl)-3-(tetrahydropyran-2-yloxy)prop-1-trans-enyl]-5α-(tetrahydropyran-2-yloxy) cyclopenteno[b]furan as a gum, $R_F = 0.76$ (75% v/v ethyl acetate/methylene chloride).

To a solution of the epimeric bis-tetrahydropyranyl ethers (399 mg.) in dry toluene (20 ml.) under an argon atmosphere at −78° C. was added di-isobutyl aluminium hydride (1.05 ml. of a 2M solution in toluene). After 10 minutes the reaction was quenched by the dropwise addition of methanol (1 ml.), and allowed to warm to room temperature. This solution was partitioned between ethyl acetate and brine, the ethyl acetate solution was separated and dried, and the solvent was evaporated to give a mixture of epimers of the bis-(tetrahydropyranyl ether) lactol, 2,3,3aβ,6aβ-tetrahydro-2-hydroxy-4β-[3-(trans-3-phenylcyclobutyl)-3-(tetrahydropyran-2-yloxy)prop-1-trans-enyl]5α-(tetrahydropyran-2-yloxy)-cyclopenteno[b]furan, $R_F = 0.42$ (3:2 v/v ethyl acetate/methylene chloride).

A mixture of (4-carboxybutyl)triphenylphosphonium bromide (7.35 g.) and potassium t-butoxide (4.0 g.) in toluene (48.6 ml.) was stirred at 90° C. under argon for 40 minutes to give an orange red solution of ylid. 7.2 Ml. of this ylide solution were added to a solution of the bis-(tetrahydropyranyl ether) lactol (298 mg.) in dry toluene under argon. After 10 minutes at room temperature, the toluene was evaporated, and water (5 ml.) was added to the residue. This aqueous solution was extracted with ether (6 × 10 ml.), acidified with oxalic acid and re-extracted with 1:1 ether/pentane. This extract was dried, and the solvent was evaporated to give 9α-hydroxy-15-(trans-3-phenylcyclobutyl)-11α,15-bis(-tetrahydropyran-2-yloxy)-16,17,18,19,20-pentanor-5-cis,13-trans-prostadienoic acid as an oil, $R_F = 0.25$ (silica gel, 5% v/v methanol in methylene chloride).

EXAMPLE 2

Methyl 15-hydroxy-9α,11α-di-(4-phenylbenzoyloxy)-15-(cis-3-phenylcyclobutyl)-16,17,18,19,20-pentanor-5-cis,13-trans-prostadienoate (310mg.) was stirred at room temperature under argon in a mixture of acetone (6ml.) and water (3ml.) with powdered potassium hydroxide (150mg.) for 16 hours. The solvent was evaporated under reduced pressure and the residue was dissolved in water (3ml.) and acidified to pH 1 by the dropwise addition of 1N hydrochloric acid. The aqueous phase was extracted with ethyl acetate (3 × 10ml.) and the combined ethyl acetate solutions were washed with brine, dried over magnesium sulphate and evaporated to dryness under reduced pressure to give a white solid residue consisting of 4-phenylbenzoic acid and a mixture of the C-15 epimers of 9α,11α,15-trihydroxy-15-(cis-3-phenylcyclobutyl)-16,17,18,19,20-pentanor-5-cis,13-trans-prostadienoic acid. The epimers were separated by preparative layer chromatography on silica gel, $R_F = 0.25$ and 0.38 (3% v/v acetic acid in ethyl acetate). The n.m.r. spectrum of each epimer in hexadeuterioacetone showed the following characteristic features (δ values):-

7.25, 5H, singlet, aromatic protons
5.2–5.7, 4H, multiplet, olefinic protons
4.0–5.0, 4H, multiplet, 4 × —O$\underline{H}$
3.8–4.25, 3H, multiplet, 3 × <$\underline{CH}$(OH)

The mass spectrum of the tetra(trimethylsilyl) derivative of the more polar epimer had M = 702 (calculated for $C_{37}H_{66}O_5Si_4 = 702$) and (M-methyl)⊕ = 687.3769 (calculated for $C_{36}H_{63}O_5Si_4 = 687.3749$).

The methyl 15-hydroxy-9α,11α-di-(4-phenylbenzoyloxy)-15-(cis-3-phenylcyclobutyl)-16,17,18,19,20-pentanor-5-cis,13-trans-prostadienoate used as the starting material was prepared as follows:-

Ethyl cis-3-phenylcyclobutanecarboxylate was converted to dimethyl 2-oxo-2-(cis-3-phenylcyclobutyl)-ethylphosphonate by the process described in Example 1. $R_F = 0.18$ (4:1v/v ethyl acetate/toluene). The n.m.r. spectrum in deuteriochloroform showed the following characteristic signals (δ values):-

7.20, 5H, singlet, aromatic protons
3.75, 6H, doublet, ($C\underline{H}_3O)_2PO$.-
3.05, 2H, doublet, —CO.$C\underline{H}_2$.PO<

A solution of the phosphonate (210mg.) and methyl 7-[2β-formyl-3α,5α-di(4-phenylbenzoyloxy)-cyclopent-1α-yl]hept-5-cis-enoate (315mg.) in 9:1 v/v toluene/t-butanol (12ml.) was stirred at room temperature under argon. A 1N aqueous solution of sodium hydroxide (0.650ml.) was added, and stirring was continued for 16 hours. 1N Aqueous hydrochloric acid (0.650ml.) was then added and the reaction mixture was partitioned between ethyl acetate (2 × 20ml.) and water (5ml.). The combined ethyl acetate solutions were dried over magnesium sulphate, and the solvent was evaporated under reduced pressure. The residue was chromatographed on "Florisil" (25g.), eluting with 9:1 v/v toluene/ethyl acetate, to give the enone, methyl 15-oxo-9α,11α-di(4-phenylbenzoyloxy)-15-(cis-3-phenylcyclobutyl)-16,17,18,19,20-pentanor-5-cis,13-trans-prostadienoate, $R_F = 0.53$ (9:1 v/v toluene/ethyl acetate).

The enone (380mg.) was stirred at room temperature under argon with a 0.36M solution of di-isobornyloxyaluminium isopropoxide in toluene (8ml.). Two hours after the starting material had completely dissolved, the mixture was partitioned between water (5ml.) and ethyl acetate (5ml.), and filtered through "Hyflo" (trade mark) kieselguhr, washing the filter pad with ethyl acetate (2 × 5ml.). The organic layer was dried over magnesium sulphate and filtered, and the solvent was evaporated to leave a crude oily product, which was chromatographed on "Florisil" (trade mark)(5g.), eluting initially with toluene to give isoborneol and then with ethyl acetate to give the enol, methyl 15-hydroxy-9α,11α-di-(4-phenylbenzoyloxy)-15-(cis-3-phenylcyclobutyl)-16,17,18,19,20-pentanor-5-cis,13-trans-prostadienoate, $R_F = 0.14$ (9:1 v/v toluene/ethyl acetate).

EXAMPLE 3

Methyl 15-[trans-3-(4-chlorophenyl)cyclobutyl]-15-hydroxy-9α,11α-di-(4-phenylbenzoyloxy)-16,17,18,19,20-pentanor-5-cis, 13-trans-prostadienoate was converted by the process described in Example 2 into a mixture of the C-15 epimers of 15-[trans-3-(4-chlorophenyl)cyclobutyl]-9α,11α,15-trihydroxy-16,17,18,19,20-pentanor-5-cis,13-trans-prostadienoic acid. The epimers were separated by preparative layer chromatography on silica gel, $R_F = 0.30$ and 0.42 (3% v/v acetic acid in ethyl acetate). The n.m.r. spectrum of each epimer in hexadeuterioacetone showed the following characteristic features (δ values):-

7.28, 4H, singlet, aromatic protons
5.1–5.7, 4H, multiplet, olefinic protons
3.9–4.6, 7H, multiplet, 3 × °$C\underline{H}$(OH) + 4 × —OH
3.2–3.6, 1H, multiplet, Aryl$C\underline{H}$<

The mass spectrum of the tetra(trimethylsilyl) derivative of the more polar epimer had M⊕ = 736 (Calculated for $C_{37}H_{65}O_5Si_4Cl = 736$) and (M-methyl)⊕ = 721.3375 (Calculated for $C_{36}H_{62}O_5Si_4Cl = 721.2263$).

Methyl 15-[cis-3-(4-chlorophenyl)cyclobutyl]-15-hydroxy-9α,11α-di-(4-phenylbenzoyloxy)-16,17,18,19,20-pentanor-5-cis,13-trans-prostadienoate was similarly converted into a mixture of the C-15 epimers of 15-[cis-3-(4-chlorophenyl)cyclobutyl]-9α,11α,15-trihydroxy-16,17,18,19,20-pentanor-5-cis,13-trans-prostadienoic acid. The epimers were separated by preparative layer chromatography on silica gel, $R_F = 0.25$ and 0.36 (3% v/v acetic acid in ethyl acetate). The n.m.r. spectrum of each epimer in hexadeuterioacetone showed the following characteristic features (δ values):-

7.28, 4H, singlet, aromatic protons
5.1–5.7, 4H, multiplet, olefinic protons
3.7–4.8, 7H, multiplet, 3 × —$C\underline{H}$(OH) + 4 × O$\underline{H}$
3.2–3.6, 1H, multiplet, Aryl$C\underline{H}$<

The mass spectrum of the tetra(trimethylsilyl) derivative of the more polar epimer had M⊕ = 736 (Calculated for $C_{37}H_{65}O_5Si_4Cl = 736$) and (M-methyl)⊕ = 721.3367 (Calculated for $C_{36}H_{62}O_5Si_4Cl = 721.3363$).

The two isomers of methyl 15-[3-(4-chlorophenyl) cyclobutyl]-15-hydroxy-9α,11α-di-(4-phenylbenzoyloxy)-16,17,18,19,20-pentanor-5-cis,13-trans-prostadienoate used as starting materials may be prepared as follows:-

Diethyl 4-chlorophenylmalonate was converted into a mixture of the cis and trans isomers of 3-(4-chlorophenyl)cyclobutanecarboxylic acid using the known procedure described by C. Beard and A. Burger, J. Org. Chem., 1962, 27, 1647 for the unsubstituted analogue. This cis-trans mixture was converted by the process described in Example 1 into a mixture of the cis and trans isomers of methyl 3-(4-chlorophenyl)cyclobutanecarboxylate, b.p. 105°–110° C. /0.05 mm. Hg.

n-Butyl lithium (16.2 ml. of a 1.23M solution in hexane) was added dropwise to a stirred solution of dimethyl methylphosphonate (2.48 g.) in dry tetrahydrofuran (25ml.) at −78° C. in an atmosphere of argon. After 10 minutes, a solution of methyl 3-(4-chlorophenyl)-cyclobutanecarboxylate mixed isomers (2.24g.) in dry tetrahydrofuran (25ml.) was added dropwise, and stirred at −78° C. for 2 hours. The reaction mixture was warmed to room temperature and neutralised by the addition of 1N hydrochloric acid (20ml.) to the stirred solution. The tetrahydrofuran was evaporated, and the residue was partitioned between ethyl acetate and water. The ethyl acetate extract was dried over sodium sulphate and the solvent was evaporated. The crude product was purified by dry column chromatography on "Kieselgel 60" (100g.) eluting with ethyl acetate, to give dimethyl 2-[3-(4-chlorophenyl)-cyclobutyl]-2-oxoethylphosphonate, as a mixture of cis and trans isomers, $R_F = 0.35$ and 0.40 (ethyl acetate). The n.m.r. spectrum in deuteriochloroform showed the following characteristic signals (δ values):-

7.0–7.3, 4H, double doublet, aromatic protons
3.73, 6H, doublet, —PO(OC$\underline{H}_3$)$_2$
3.3–3.6, 1H, multiplet, ArylC$\underline{H}$<

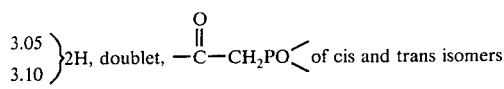
3.05, 3.10 } 2H, doublet, —C(=O)—CH$_2$PO< of cis and trans isomers

A solution of the phosphonate (222mg.) and methyl 7-[2β-formyl-3α,5α-di(4-phenylbenzoyloxy)cyclopent-1α-yl]-hept-5-cis-enoate (340mg.) in 9:1 v/v toluene/t-butanol (8ml.) was stirred at room temperature under argon. A 1N aqueous solution of sodium hydroxide (0.650ml.) was added, and stirring was continued for 16 hours. 1N Aqueous hydrochloric acid (0.650ml.) was then added, and the reaction mixture was partitioned between ethyl acetate (2 × 20ml.) and water (5ml.). The ethyl acetate solutions were combined and dried over sodium sulphate, and the solvent was evaporated under reduced pressure. Preparative layer chromatography of the residue or silica gel, eluting twice with 9:1 v/v toluene/ethyl acetate gave the separated cis and trans isomers of the enone, methyl 15-[3-(4-chlorophenyl)cyclobutyl]-15-oxo-9α,11α-di-(4-phenylbenzoyloxy)-16,17,18,19,20-pentanor-5-cis,13-trans-prostadienoate, $R_F = 0.43$ and 0.47 (4:1 v/v toluene/ethylacetate).

Each enone isomer was reduced to the required 15-hydroxy starting material by reduction with di-isobornyloxyaluminium isopropoxide by the process described in Example 2.

EXAMPLE 4

The processes described in Example 3 were repeated using a mixture of cis and trans isomers of ethyl 3-(3-tolyl)cyclobutanecarboxylate in place of methyl 3-(4-chlorophenyl)cyclobutanecarboxylate to give the separated cis- and trans- cyclobutyl isomers of 9α,11α,15-trihydroxy-15-[3-(3-tolyl)cyclobutyl]-16,17,18,19,20-pentanor-5-cis, 13-trans-prostadienoic acid, each as separated C-15 epimers.

The cis-cyclobutyl isomer had $R_F = 0.29$ and 0.45 (3% v/v acetic acid in ethyl acetate). The n.m.r. spectrum of each epimer in hexadeuterioacetone showed the following characteristic features (δ values):-

6.8–7.2, 4H, multiplet, aromatic protons
5.0–5.6, 4H, multiplet, olefinic protons
3.5–4.8, 7H, multiplet, 3 × >C$\underline{H}$(OH) + 4 × O$\underline{H}$
3.1–3.5, 1H, multiplet, ArylC$\underline{H}$<
2.25, 3H, singlet, ArylC$\underline{H}_3$ The mass spectrum of the tetra(trimethylsilyl) derivative of the more polar epimer had $M^\oplus = 716$ (calculated for $C_{38}H_{68}O_5Si_4 = 716$) and (M-methyl)$^\oplus$ 701.3929 (calculated for $C_{37}H_{65}O_5Si_4 = 701.3909$).

The trans-cyclobutyl isomer had $R_F = 0.30$ and 0.46 (3% v/v acetic acid in ethyl acetate). The n.m.r. spectrum of each epimer in hexadeuterioacetone showed the following characteristic features (δ values):-

6.8–7.2, 4H, multiplet, aromatic protons
5.1–5.6, 4H, multiplet, olefinic protons
3.7–5.0, 7H, multiplet, 3 × <C$\underline{H}$(OH) + 4 × O$\underline{H}$
3.2–3.6, 1H, multiplet, Aryl C$\underline{H}$<
2.25, 3H, singlet, ArylC$\underline{H}_3$ The mass spectrum of the tetra(trimethylsilyl) derivative of the more polar epimer had $M^\oplus = 716$ (calculated for $C_{38}H_{68}O_5Si_4 = 716$) and (M-methyl)$^\oplus = 701.3874$ (calculated for $C_{37}H_{65}O_5Si_4 = 701.3905$).

The mixture of cis and trans isomers of ethyl 3-(3-tolyl)cyclobutanecarboxylate used as starting material was prepared as follows:- n-Butyl lithium (1.74ml. of a 1.23M solution in hexane) was added dropwise to a stirred solution of diisopropylamine (0.300ml.) in dry tetrahydrofuran at −78° C. in an atmosphere of argon. The solution was warmed to 0° C. and stirred during the dropwise addition of a solution of ethyl cis-3-(3-tolyl)cyclobutanecarboxylate (465mg.). After 90 minutes at 0° C., the reaction was quenched by the addition of water (1ml.). The tetrahydrofuran was evaporated under reduced pressure, and the residue was dissolved in ethyl acetate (20ml.). The ethyl acetate solution was washed with 1N hydrochloric acid (5ml.), followed by saturated aqueous brine (5ml.) and dried over sodium sulphate. The ethyl acetate was evaporated under reduced pressure, and the residue was finally dried by azeotropic evaporation of added dry toluene under reduced pressure, to give a mixture of the cis and trans isomers of ethyl 3-(3-tolyl)-cyclobutanecarboxylate.

EXAMPLE 5

The process described in Example 3 was repeated using the appropriate 3-substituted cyclobutanecarboxylic ester to give the compounds shown below. In some examples the cis- and trans-cyclobutyl isomers were separated at the enone stage. In the other examples the final prostaglandin analogue was obtained as a mixture of cis- and trans-cyclobutyl isomers. The prostaglandin products were identified by n.m.r. spectroscopy and are characterised below by accurate mass measurement by mass spectrometry of the molecular ion or the (M-methyl)$^\oplus$ ion, whichever is more appropriate, of the tetra(trimethylsilyl) derivative. The phosphonate reagent and the enone intermediate of the formula XI (wherein $R^1$ is a methoxycarbonyl radical, $R^2$ is a hydrogen atom, $R^{12}$ and $R^{13}$ are 4-phenylbenzoyloxy radicals and X is a cis-vinylene radical) were identified by n.m.r. spectroscopy and characterised by the $R_F$ values given below.

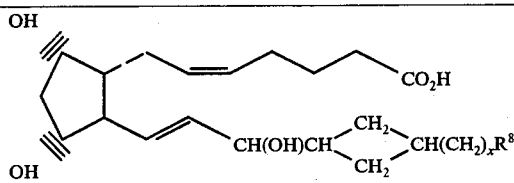

| No. | x | R$_8$ | Isomer | | R$_F$ (a) | Mass spectrum of more polar epimer | | Phosphonate R$_F$(b) | Enone R$_F$ |
|---|---|---|---|---|---|---|---|---|---|
| | | | | | | Found | Calculated | | |
| 1 | 0 | 3-trifluoro-methylphenyl | cis-cyclobutyl | m.p. l.p. | 0.34 0.48 | M$^\oplus$ = 770 (M-methyl)$^\oplus$ = 755.3583 | 770 755.3624 | 0.40 | 0.63(c) |
| 2 | 0 | 4-methoxy-phenyl | cis/trans-cyclobutyl mixture | m.p. l.p. | 0.18 0.26 | M$^\oplus$ = 717.3885 | 717.3858 | 0.28 | 0.41(d) |
| 3 | 0 | 4-fluorophenyl | cis/trans-cyclobutyl mixture | m.p. l.p. | 0.32 0.45 | M$^\oplus$ = 720 (M-methyl)$^\oplus$ = 705.3650 | 720 705.3659 | 0.47 | 0.34(d) |
| 4 | 0 | 1-naphthyl | trans-cyclobutyl | m.p. l.p. | 0.47 0.55 | M$^\oplus$ = 752 (M-methyl)$^\oplus$ = 737.3890 | 752 737.3909 | }0.28 | 0.65(c) |
| 5 | 0 | 1-naphthyl | cis-cyclobutyl | m.p. l.p. | 0.43 0.52 | M$^\oplus$ = 752 (M-methyl)$^\oplus$ = 737.3970 | 752 737.3909 | | 0.63(c) |
| 6 | 1 | phenyl | cis/trans-cyclobutyl mixture | m.p. l.p. | 0.45 0.57 | M$^\oplus$ = 716.4124 | 716.4140 | 0.30 | 0.65(c) |
| 7 | 2 | phenyl | cis/trans-cyclobutyl mixture | m.p. l.p. | 0.31 0.50 | M$^\oplus$ = 730 (M-Me$_3$SiOH)$^\oplus$ = 640.3796 | 730 640.3800 | 0.31 | 0.81(e) | m.p. = more polar isomer
l.p. = less polar isomer
(a) solvent system 3% v/v acetic acid in ethyl acetate
(b) solvent system ethyl acetate
(c) solvent system 4:1 v/v toluene/ethyl acetate
(d) solvent system 9:1 v/v toluene/ethyl acetate
(e) solvent system 1:1 v/v toluene/ethyl acetate

EXAMPLE 6

Methyl 15-hydroxy-9α,11α-di(4-phenylbenzoyloxy)-15-(trans-3-phenylcyclobutyl)-16,17,18,19,20-pentanor-13-trans-prostenoate (132mg.) was stirred at room temperature under argon in a mixture of acetone (3ml.) and water (1ml.) with powdered potassium hydroxide (40mg.) for 16 hours. The solvent was evaporated under reduced pressure, the residue was dissolved in water (3ml.) and the solution was acidified to pH 1 by the dropwise addition of 1N hydrochloric acid. The aqueous phase was extracted with ethyl acetate (3 × 10ml.) and the combined ethyl acetate solutions were washed with brine, dried over sodium sulphate and evaporated to dryness under reduced pressure to give a white solid residue consisiting of 4-phenylbenzoic acid and a mixture of the C-15 epimers of 9α,11α,15-trihydroxy-15-(trans-3-phenylcyclobutyl-16,17,18,19,20-pentanor-13-trans-prostenoic acid. The epimers were separated by preparative layer chromatography on silica gel, R$_F$ = 0.23 and 0.34 (3% v/v acetic acid in ethyl acetate). The n.m.r. spectrum of each epimer in hexadeuterioacetone showed the following characteristic features (δ values):-

7.28, 5H, singlet, aromatic protons
5.4–5.6, 2H, multiplet, trans-olefinic protons
3.5–5.5, 7H, multiplet, 3 × <C$\underline{H}$(OH) + O$\underline{H}$
3.3–3.7, 1H, multiplet, PhC$\underline{H}$<

The mass spectrum of the tetra(trimethylsilyl) derivative of the more polar epimer had M$\oplus$ = 704.4107 (calculated for C$_{37}$H$_{68}$O$_5$Si$_4$ = 704.4144).

The methyl 15-hydroxy-9α,11α-di(4-phenylbenzoyloxy)-15-(trans-3-phenylcyclobutyl)-16,17,18,19,20-pentanor-13-trans-prostenoate used as starting material may be prepared as follows:-

A solution of a mixture of the cis and trans isomers of dimethyl 2-oxo-2-(3-phenylcyclobutyl)ethylphosphonate (406mg.) and methyl 7-[2β-formyl-3α,5α-di(4-phenylbenzoyloxy)-cyclopent-1α-yl]heptanoate (500mg.) in 9:1 v/v toluene/t-butanol (15ml.) was stirred at room temperature under argon. A 1N aqueous solution of sodium hydroxide (1.28ml.) was added and stirring was continued for 16 hours. Glacial acetic acid (0.077ml.) was then added, and the reaction mixture was partitioned between ethyl acetate (2 × 25ml.) and brine (5ml.). The ethyl acetate solution was dried over sodium sulphate, and the solvent was evaporated under reduced pressure. The residue was chromatographed on a dry column of "Kieselgel 60" (260g.), eluting with 5% v/v ethyl acetate in toluene, to yield the enone, methyl 15-oxo-9α,11α-di(4-phenylbenzoyloxy)-15-(trans-3-phenylcyclobutyl)-16,17,18,19,20-pentanor-13-trans-prostenoate, R$_F$ = 0.65 (9:1 toluene/ethyl acetate), plus the corresponding cis isomer, R$_F$ = 0.60.

The enone (140mg.) was stirred at room temperature under argon with a 0.36M solution of di-isobornyloxy aluminium isopropoxide in toluene (3ml.). Three hours after the starting material had completely dissolved, the mixture was partitioned between water (5ml.) and ethyl acetate (5ml.), and filtered through "Hyflo", washing the filter pad with ethyl acetate (2 × 5ml.). The organic layer was dried over sodium sulphate, filtered and the solvent was evaporated to leave a crude oily product, which was chromatographed on "Florisil" (5g.), eluting initially with toluene to give isoborneol, and then with ethyl acetate to give the required enol starting material, methyl 15-hydroxy-9α,11α-di(4-phenylbenzoyloxy)-15-(trans-3-phenylcyclobutyl)-16,17,18,19,20-pentanor-13- trans-prostenoate, $R_F = 0.07$ (9:1 toluene/ethyl acetate).

EXAMPLE 7

The process described in Example 2 was repeated, using methyl 15-hydroxy-9α,11α-di(3-phenylbenzloxy-15-(trans-3-phenylcyclobutyl)-16,17,18,19,20-pentanor-5-cis-prostenoate, in place of methyl 15-hydroxy-9α,-11α-di(4-phenylbenzoyloxy)-15-(cis-3-phenylcyclobutyl)-16,17,18,19,20-pentanor-5-cis, 13-trans-prostadienoate, to give a mixture of the C-15 epimers of 9α,11α,15-trihydroxy-15-(trans-3-phenylcyclobutyl)-16,17,18,19,20-pentanor-5-cis-prostenoic acid, $R_F = 0.4$ (3% acetic acid in ethyl acetate). The n.m.r. spectrum in hexadeuterioacetone showed the following characteristic features (δ values):-

7.25, 5H, singlet, aromatic protons
3.4–3.6, 2H, multiplet, cis-olefinic protons
3.8–4.2, 3H, multiplet, 3 × >CH(OH)

The mass spectrum of the tetra(trimethylsilyl) derivative had M⊕ = 704 (calculated for $C_{37}H_{68}O_5Si_4 = 704$) and (M-methyl)⊕ = 689.3864 (calculated for $C_{36}H_{65}O_5Si_4 = 689.3905$).

The methyl 15-hydroxy-9α,11α-di(4-phenylbenzloxy)-15-(trans-3-phenylcyclobutyl)-16,17,18,19,20-pentanor-5-cis-prostenoate used as starting material may be prepared as follows:-

Methyl 7-[2β-formyl-3α,5α-di(4-phenylbenzoyloxy)-cyclopent-1α-yl]hept-5-cis-enoate was converted to the enone, methyl 15-oxo-9α,11α-di(4-phenylbenzoyloxy)-15-(trans-3-phenylcyclobutyl-16,17,18,19,20-pentanor-5-cis-prostenoate, by the process described in the second part of Example 6.

A solution of the enone (40mg.) in dry 1,2-dimethoxyethane (2ml.) was stirred under argon with sodium borohydride (20mg.) for 40 minutes. The reaction mixture was acidified by the dropwise addition of 1N hydrochloric acid and the 1,2-dimethoxyethane was evaporated under reduced pressure. The residue was extracted with ethyl acetate (10ml.). The ethyl acetate solution was dried over sodium sulphate, and evaporated to dryness under reduced pressure. The residue consisted of a mixture of the required starting material, methyl 15-hydroxy-9α,11α-di-(4-phenylbenzoyloxy)-15-(trans-3-phenylcyclobutyl)-16,17,18,19,20-pentanor-5-cis-prostenoate and the corresponding Δ 13 compound. Preparative layer chromatography of this mixture on silica gel plates (previously saturated with a 4% w/v solution of silver nitrate in 1:1 v/v water/methanol and baked at 100° C. for 30 minutes) eluting once with 9:1 v/v toluene/ethyl acetate and once with 3:1 v/v toluene/ethyl acetate, gave the required 5-cis-prostenoate, $R_F = 0.31$.

EXAMPLE 8

A mixture of cis- and trans-cyclobutyl isomers of methyl 15-hydroxy-15-(1-methyl-3-phenylcyclobutyl)-9α,11α-di(4-phenylbenzoyloxy)-16,17,18,19,20-pentanor-5-cis,13-trans-prostadienoate was hydrolysed by the process described in Example 2 to give the separated C-15 epimers of 9α,11α,15-trihydroxy-15-(1-methyl-3-phenylcyclobutyl)-16,17,18,19,20-pentanor-5-cis,13-trans-prostadienoic acid, $R_F = 0.27$ and 0.43 (3% v/v acetic acid in ethyl acetate). The n.m.r. spectrum of each epimer in hexadeuterioacetone showed the following characteristic features (δ values):-

7.25, 5H, singlet, aromatic protons
5.1–6.2, 8H, multiplet, 4 × olefinic protons + 4 × —OH
3.8–4.2, 3H, multiplet, 3 × >CH(OH)

1.10, 1.24 }3H, singlets, —CH₃ of cis and trans isomers

The mass spectrum of the tetra(trimethylsilyl) derivative of the more polar epimer had M⊕ = 716 (calculated for $C_{38}H_{68}O_5Si_4 = 716$) and (M-methyl)⊕ = 701.3887 (calculated for $C_{37}H_{65}O_5Si_4 = 701.3905$).

The methyl 15-hydroxy-15-(1-methyl-3-phenylcyclobutyl)9α, 11α-di-(4-phenylbenzoyloxy)-16,17,18,19,20-pentanor-5-cis, 13-trans-prostadienoate used as starting material was prepared as follows:

n-Butyl lithium (8.15ml. of a 1.23M solution in hexane) was added dropwise to a stirred solution of di-isopropylamine (1.40ml.) in dry tetrahydrofuran (15ml.) at −78° C. in an atmosphere of argon. The solution was warmed to 0° C. and a solution of methyl 3-phenylcyclobutanecarboxylate (1.90g.) in dry tetrahydrofuran (20ml.) was added dropwise and the reaction mixture was stirred at 0° C. for 1 hour. Methyl iodide (1.30ml.) was added and stirring was continued for 16 hours, allowing the reaction mixture to warm to room temperature. The tetrahydrofuran was evaporated under reduced pressure and the residue was partitioned between ethyl acetate (2 × 20ml.) and 0.5N hydrochloric acid (10ml.). The ethyl acetate solution was dried over sodium sulphate and the solvent was evaporated under reduced pressure to give the ester, methyl 1-methyl-3-phenylcyclobutanecarboxylate as a 2:1 mixture of isomers. The n.m.r. spectrum is deuteriochloroform showed the following characteristic features (δ values):

7.25, 5H, singlet, aromatic protons 3.74, 3.70, }3H, singlets, —CO₂CH₃ of cis and trans isomers 3.3–3.7, 1H, multiplet, PhCH<

1.50, 1.34, }3H, singlets, —CH₃ of cis and trans isomers

The above ester was converted, via the corresponding phosphonate and enone, by the process described in Example 2, into methyl 15-hydroxy-15-(1-methyl-3-phenylcyclobutyl)-9α,11α-di(4-phenylbenzoyloxy)-16,17,18,18,20-pentanor-5-cis,13-trans-prostadienoate.

EXAMPLE 9

Methyl 15-hydroxy-9α,11α-di(4-phenylbenzoyloxy)-15-(trans-4-phenylcyclohexyl)-16, 17,18,19,20-pentanor-5-cis, 13-trans-prostadienoate was converted by the process described in Example 2 into the separate C-15 epimers of 15-(trans-4-phenylcyclohexyl)-9α,11α,15-trihydroxy-16,17,18,19,20-pentanor-5-cis,13-trans-prostadienoic acid $R_F = 0.29$ and 0.47 (3% v/v acetic acid in ethyl acetate). The n.m.r. spectrum of each epimer showed the following characteristic features (δ values):-

7.20, 5H, singlet, aromatic protons
5.2–5.8, 4H, multiplet, olefinic protons
4.0–4.9, 4H, multiplet, 4 × -OH

4.05–4.2, 1H, multiplet,  
3.8–4.0, 2H, multiplet,  } 3 × >CH(OH)

The mass spectrum of the tetra(trimethylsilyl) derivative of the more polar epimer had $M^\oplus$ = 730.4242, (calculated for $C_{39}H_{70}O_5Si_4$ = 730.4296).

The 15-hydroxy compound used as the starting material was prepared as follows:- trans-4-Phenylcyclohexanecarboxylic acid was converted to the corresponding methyl ester by treatment with excess ethereal diazomethane.

The process described in the second part of Example 2 was repeated, using this ester, methyl trans-4-phenylcyclohexylcarboxylate, in place of ethyl cis-3-phenylcyclobutanecarboxylate, to give the required 15-hydroxy starting material.

EXAMPLE 10

Methyl 15-[trans-3-(4-biphenylyl)cyclobutyl]-15-hydroxy-9α,11α-di(4-phenylbenzoyloxy)-16,17,18,19,20-pentanor-5-cis,13-trans-prostadienoate(70mg.) was stirred at room temperature under argon in a mixture of anhydrous methanol (3ml.) and anhydrous methylene chloride (0.15ml.) with powdered potassium carbonate (46mg.) for 16 hours. 2N-Hydrochloric acid (0.40ml.) and saturated brine (2ml.) was added, and the mixture was extracted with ethyl acetate (2 × 10ml.). The combined ethyl acetate solutions were dried over magnesium sulphate, and the solvent was evaporated under reduced pressure. Preparative layer chromatography of the residue gave the separated C-15 epimers of methyl 15 [trans-3-(4-biphenylyl)cyclobutyl]-9α,11α,15-trihydroxy-16,17,18,19,20-pentanor-5-cis,13-trans-prostadienoate, $R_F$ = 0.21 and 0.35 (ethyl acetate). The n.m.r. spectrum of each epimer in hexadeuterioacetone showed the following characteristic features (δ values):-

7.1–7.7, 9H, multiplet, aromatic protons  
5.2–5.7, 4H, multiplet, olefinic protons 4.1–4.3, 2H, multiplet,  
3.85–4.1, 1H, multiplet,  } 3 × >CH(OH)

3.63, 3H, singlet, -CO$_2$CH$_3$  
3.4–3.75, 1H, multiplet, ArylCH<

The mass spectrum of the tris(trimethylsilyl) derivative of the more polar epimer had $M^\oplus$ = 720 (calculated for $C_{41}H_{64}O_5Si_3$ = 720) and M-methyl)$^\oplus$ = 705.3819 (calculated for $C_{40}H_{61}O_5Si_3$ = 705.3823).

By the same process methyl 15-[cis-3-(4-biphenylyl)cyclobutyl]-15-oxo-9α,11α-(4-phenylbenzoyloxy)-16,17,18,19,20-pentanor-5-cis,13-trans-prostadienoate was converted into the separated C-15 epimers of methyl 15-[cis-3-(4-biphenylyl)-cyclobutyl]-9α,11α,15-trihydroxy-16,17,18,19,20-pentanor-5-cis,13-trans-prostadienate $R_F$ = 0.21 and 0.36 (ethyl acetate). The n.m.r. spectrum of each epimer in hexdeuterioacetone showed the following characteristic signals (δ values):-

7.1–7.7, 9H, multiplet, aromatic protons  
5.2–5.7, 4H, multiplet, olefinic protons 4.10–4.25, 1H, multiplet  
3.85–4.10, 2H, multiplet  } 3 × >CH(OH)

3.65, 3H, singlet, -CO$_2$CH$_3$  
3.2–3.5, 1H, multiplet, ArylCH<

The mass spectrum of the tris(trimethylsilyl) derivative of the more polar epimer had $M^\oplus$ = 720.4016 (calculated for $C_{41}H_{64}O_5Si_3$ = 720.4062).

The trans and cis isomers of methyl 15-[3-(4-biphenylyl)cyclobutyl]-15-hydroxy-9α,11α-di-(4-phenylbenzoyloxy)-16,17,18,19,20-pentanor-5-cis,13-trans-prostadienoate used as starting materials were prepared as follows:-

Fuming nitric acid (0.54ml.) was added dropwise to a stirred solution of methyl 3-phenylcyclobutanecarboxylate (950mg.) in acetic anhydride (5ml.) and glacial acetic acid (0.25ml.) at −5° C. The reaction mixture was set aside overnight at room temperature then poured onto ice and extracted with ethyl acetate (3 × 20ml.) The ethyl acetate solution was dried over magnesium sulphate and evaporated under reduced pressure. Chromatography of the residue on a column of "Florisil" (25g.), eluting with toluene, gave methyl 3-(4-nitrophenyl)cyclobutanecarboxylate as a pale yellow oil. The n.m.r. spectrum in deuteriochloroform showed the following characteristic signals (δ values):-

8.15, 2H, doublet,  
7.40, 2H, doublet,  } aromatic protons 3.80, 3H, singlet, —OCH$_3$ A solution of this nitro compound (750mg.) in ethyl acetate (20ml.) was stirred for 16 hours with a 5% palladium on carbon catalyst (250mg.) in an atmosphere of hydrogen. The solution was filtered through a pad of "Hyflo" and evaporated to give methyl 3-(4-aminophenyl)-cyclobutanecarboxylate. A solution of this amine (800mg.) in dry benzene (20ml.) was stirred under argon at room temperature during the dropwise addition of amyl nitrite (0.755ml.). The temperature of the reaction mixture was slowly (over 2½ hours) raised to its boiling point and the mixture was then refluxed for 1 hour. The solvent was evaporated under reduced pressure and the residue was chromatographed on a dry column of silica gel 'MFC' (supplied commercially by Hopkin and Williams) (25g.), eluting with toluene to give a mixture of cis and trans isomers of methyl 3-(4-biphenylyl)cyclobutanecarboxylate, $R_F$ = 0.70 (9:1 v/v toluene/ethyl acetate). The n.m.r. spectrum in deuteriochloroform showed the following characteristic features (δ values):-

7.1–7.7, 9H, multiplet, aromatic protons 3.76,  
3.83,  } 3H, singlets, —CO$_2$CH$_3$ of cis and trans isomers This ester was converted by the process described in Example 3 into the separated trans and cis isomers of the enone, methyl 15-[3-(4-biphenylyl)cyclobutyl]-15-oxo- 9α,11α-di-(4-phenylbenzoyloxy)-16, 17, 18, 19, 20-pentanor-5-cis, 13-trans-prostadienoate, $R_F$ = 0.55 and 0.60 (9:1 v/v toluene/ethyl acetate, double elution).

The enone (70mg.) was stirred at room temperature under argon with a 0.36M solution of di-isobornyloxyaluminium isopropoxide in toluene (2ml.). Two hours after the starting material had completely dissolved, the mixture was partitioned between water (5ml.) and ethyl acetate (5ml.), and filtered through "Hyflo" washing the filter pad with ethyl acetate (2 × 5ml.). The organic layer was dried over magnesium sulphate and filtered, and the solvent was evaporated to leave a crude oily product, which was chromatographed on "Florisil" (4g.), eluting initially with toluene to give isoborneol, and then with ethyl acetate to give the required enol starting material, methyl 15-[trans-3-(4-biphenylyl)cyclobutyl]-15-hydroxy-9α,11α-di-(4-phenylbenzoyloxy)-16, 17, 18, 19, 20-pentanor-5-cis, 13-trans-prostadienoate, $R_F = 0.16$ (9:1 v/v toluene/ethyl acetate).

EXAMPLE 11

The process described in the first part of Example 10 was repeated, using methyl 15-hydroxy-[3-(4-nitrophenyl)-cyclobutyl]-9α,11α-di(4-phenylbenzoyloxy)-16, 17, 18, 19, 20-pentanor-5-cis, 13-trans-prostadienoate in place of the corresponding 4-biphenylyl compound, to give a mixture of cis- and trans- cyclobutyl isomers of methyl 9α,11α, 15-trihydroxy-15-[3-(4-nitrophenyl)cyclobutyl]-16, 17, 18, 19, 20-pentanor-5-cis, 13-trans-prostadienoate, separated by preparative layer chromatography on silica gel into C-15 epimers $R_F = 0.22$ and 0.35 (1% v/v acetic acid in ethyl acetate). The n.m.r. spectrum of each epimer in deuteriochloroform showed the following characteristic features (δ values):-

7.3–8.1, 4H, multiplet, aromatic protons
5.2–5.7, 4H, multiplet, olefinic protons
3.8–4.3, 3H, multiplet, 3 × > C$\underline{H}$(OH)
3.63, 3H, singlet, —CO$_2$C$\underline{H}_3$ The mass spectrum of the tris(trimethylsilyl) derivative of the more polar epimer had $M^\oplus = 689$ (calculated for $C_{35}H_{59}O_7NSi_3 = 689$) and (M-methyl)$^\oplus = 674.3366$ (calculated for $C_{34}H_{56}O_7NSi_3 = 674.3365$).

The starting material used in the above process was prepared by the sequence of reactions described in the latter part of Example 10, using methyl 3-(4-nitrophenyl)-cyclobutanecarboxylate in place of methyl 3-(4-biphenylyl)-cyclobutanecarboxylate.

EXAMPLE 12

The process described in Example 10 was repeated, using methyl 15-hydroxy-di(4-phenylbenzoyloxy)-15-(3-phenylcyclopentyl)-16, 17, 18, 19, 20-pentanor-5-cis, 13-trans-prostadienoate in place of the corresponding 3-(4-biphenylyl)-cyclobutyl starting material, to give a mixture of cis-and trans- cyclopentyl isomers of methyl 9α,11α, 15-trihydroxy-15-(3-phenylcyclopentyl)-16, 17, 18, 19, 20-pentanor-5-cis, 13-trans-prostadienoate. The C-15 epimers were separated by preparative layer chromatography on silica gel, $R_F = 0.20$ and 0.39 (1% v/v acetic acid in ethyl acetate). The n.m.r. spectrum of each epimer in deuteriochloroform showed the following characteristic features (δ values):-

7.20, 5H, singlet, aromatic protons
5.5–5.7, 2H, multiplet, trans olefinic protons
5.3–5.5, 2H, multiplet, cis-olefinic protons
3.8–4.3, 3H, multiplet, 3 × C$\underline{H}$(OH)
3.65, 3H, singlet, —CO$_2$C$\underline{H}_3$ The mass spectrum of the tris(trimethylsilyl) derivative of the more polar epimer had $M^\oplus = 658.3894$ (calculated for $C_{36}H_{62}O_5Si_3 = 658.3906$).

The epimeric mixture of cis- and trans- cyclopentyl isomers of methyl 15-hydroxy-15-(3-phenylcyclopentyl)-9α,11α-di(4-phenylbenzoyloxy)-16, 17, 18, 19, 20-pentanor-5-cis, 13-trans-prostadienoate used as the starting material was prepared by the sequence of reactions described in the second part of Example 2, using a mixture of cis and trans isomers of methyl 3- phenylcyclopentanecarboxylate (obtained by esterification of the known 3-phenylcyclopentanecarboxylic acid) in place of ethyl cis-3-phenylcyclobutanecarboxylate.

EXAMPLE 13

Powdered lithium aluminum hydride (5mg.) was added to a stirred solution of the more polar C-15 epimer of methyl 9α,11α, 15-trihydroxy-15-(trans-3-phenylcyclobutyl)-16, 17, 18, 19, 20-pentanor-5-cis, 13-trans-prostadienoate (14mg.) in anhydrous diethyl ether (2ml.) at room temperature in an atmosphere of argon. After one hour, water (0.02ml.) was added, the reaction mixture was diluted with ethyl acetate (5ml.), dried over magnesium sulphate and filtered. The filtrate was evaporated under reduced pressure, and the residue was purified by preparative chromatography on silica gel, to give the corresponding C-15 epimer of 15-(trans-3-phenylcyclobutyl)-16, 17, 18, 19, 20pentanor-5-cis, 13-trans-prostadien-1,9α,11α, 15-tetraol, $R_F = 0.10$ (3% v/v acetic acid in ethyl acetate).

The n.m.r. spectrum in hexadeuterioacetone showed the following characteristic features (δ values): -

7.25, 5H, singlet, aromatic protons
5.1–5.65, 4H, multiplet, olefinic protons

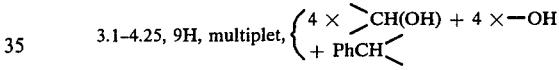

3.1–4.25, 9H, multiplet, $\begin{cases} 4 \times >CH(OH) + 4 \times -OH \\ + PhCH< \end{cases}$ The mass spectrum of the tetra(trimethylsilyl) derivative had $M^\oplus = 688.4256$ (calculated for $C_{37}H_{68}O_4Si_4 = 688.4191$).

The more polar C-15 epimer of methyl 15-(trans-3-phenylcyclobutyl)-9α,11α, 15-trihydroxy-16, 17, 18, 19, 20-pentanor-5-cis, 13-trans-prostadienoate used as starting material was prepared as follows:-

A mixture of cis and trans isomers of methyl 3-phenylcyclobutanecarboxylate was converted, by the process described in Example 3, into the enone, methyl 15-oxo-9α,11α-di-(4-phenylbenzoyloxy)-15-(trans-3-phenylcyclobutyl)-16, 17, 18, 19, 20-pentanor-5-cis, 13-trans-prostadienoate $R_F = 0.36$ (9:1 v/v toluene/ethyl acetate), which was converted by the process described at the end of Example 10 into the separated C-15 epimers of methyl 9α,11α, 15-trihydroxy-15-(trans-3-phenylcyclobutyl)-16, 17, 18, 19, 20-pentanor-5-cis, 13-trans-prostadienoate, $R_F = 0.22$ and 0.31 (ethyl acetate).

EXAMPLE 14

A solution of a mixture of cis and trans isomers of 9-oxo-15-(3-phenylcyclobutyl)-11α, 15-bis(tetrahydropyran-2-yloxy)-16, 17, 18, 19, 20-pentanor-5-cis, 13-trans-prostadienoic acid (50mg.) in a mixture of glacial acetic acid (1ml.), water (0.5ml.) and tetrahydrofuran (1ml.) was maintained at 50° C. for 5 hours in an argon atmosphere. The solvents were removed under reduced pressure with the aid of added toluene. Preparative layer chromatography of the residue on silica gel gave the separated C-15 epimers of the mixed cis and trans isomers of 11α,15-dihydroxy-9-oxo-15-(3-phenylcyclobutyl)-16,17,18,19,20-pentanor-5-cis,13-transprostadienoic acid, $R_F = 0.33$ and 0.47 (3% v/v acetic acid in ethyl acetate). The n.m.r. spectrum of the more polar epimer in hexadeuterioacetone showed the following characteristic features (δ values):-

7.20, 5H, singlet, aromatic protons
5.5–5.75, 2H, multiplet, trans-olefinic protons
5.3–5.5, 2H, multiplet, cis-olefinic protons
3.8–4.2, 2H, multiplet, 2 × > C$\underline{H}$(OH)

The mass spectrum of the tris(trimethylsilyl)-9-methoxime derivative of the more polar epimer had $M^{\oplus} = 657$ (calculated for $C_{35}H_{59}O_5NSi_3 = 657$) and $(M\text{-methyl})^{\oplus} = 642.3457$ (calculated for $C_{34}H_{56}O_5NSi_3 = 642.3463$).

The bis(tetrahydropyranyl ether) used as starting material in the above process was prepared as follows:-

A solution of a mixture of cis and trans isomers of 9α-hydroxy-15-(3-phenylcyclobutyl)-11α,15-bis(tetrahydropyran-2-yloxy)-16,17,18,19,20-pentanor-5-cis, 13-transprostadienoic acid (prepared as described in the second part of Example 1) (150mg.) in anhydrous methylene chloride (10ml.) was stirred for 1½ hours with pyridinium chlorochromate (83mg.) and powdered anhydrous sodium acetate (7mg.) at room temperature in an argon atmosphere. Methanol (0.5ml.) was added and the reaction mixture was evaporated to dryness under reduced pressure. Dry column chromatography of the residue on "Kieselgel 60", eluting with ethyl acetate, gave 9-oxo-15-(3-phenylcyclobutyl)-11α,15-bis(tetrahydropyran-2-yloxy)-16,17,18,19,20-pentanor-5-cis, 13-trans-prostadienoic acid.

EXAMPLE 15

The process described in Example 14 was repeated, using 15-(3-benzylcyclobutyl)-9-oxo-11α,15-bis(tetrahydropyran-2-yloxy)-16,17,18,19,20-pentanor-5-cis,13-trans-prostadienoic acid as the starting material, to give a mixture of C-15 epimers of the mixed cis and trans isomers of 15-(3-benzylcyclobutyl)-11α,15-dihydroxy-9-oxo-16,17,18,19,20-pentanor-5-cis,13-trans-prostadienoic acid, $R_F = 0.51$ and 0.61 (3% acetic acid in ethyl acetate). The n.m.r. spectrum in hexadeuterioacetone showed the following characteristic features (δ values):-

7.15, 5H, singlet, aromatic protons
5.5–6.6, 3H, multiplet, 3 x -OH
5.5–5.7, 2H, multiplet, trans-olefinic protons
5.25–5.4, 2H, multiplet, cis-olefinic protons
3.8–4.2, 2H, multiplet, 2 × < C$\underline{H}$(OH)

The mass spectrum of the tris(trimethylsilyl)-9-methoxime derivative had $M^{\oplus} = 671$ (calculated for $C_{36}H_{61}O_5NSi_3 = 671$) and $(M\text{-methyl})^{\oplus} = 656.3610$ (calculated for $C_{35}H_{58}O_5NSi_3 = 656.3619$).

The 9-oxo-bis(tetrahydropyranyl)ether used as the starting material was prepared as follows:-

Diethyl benzylmalonate (100g.) was added dropwise to a stirred suspension of lithium aluminimum hydride (12g.) in anhydrous diethyl ether (300ml.) at 0° C. under argon. The reaction mixture was then stirred overnight at room temperature and worked up by the conventional procedure, described in J. Org. Chem. 1953, 18, 1190. Evaporation of the ether solution gave 2-benzyl-propane-1,3-diol. Phosphorus tribromide (26ml.) was added dropwise to this diol (44g.), whilst stirring at 75° C. After the vigorous reaction had ceased, the temperature was raised to 100° C. and maintained at this temperature overnight. The cooled mixture was poured into ice water (500ml.) and extracted with diethyl ether (2 × 500ml.). The combined ether extracts were washed with aqueous sodium bicarbonate, then brine, dried over sodium sulphate and the ether was evaporated. Distillation of the crude product in vacuo gave 2-benzyl-1,3-dibromopropane b.p. 116°–121° C./1.0 mm. Hg.

A solution of dibromide (58.5g.) and diethyl malonate (32g.) in absolute ethanol (200ml.) was stirred under reflux during the dropwise addition of a solution of sodium ethoxide, prepared from sodium metal (9.2g.) and absolute ethanol (200ml.). Stirring was continued overnight under reflux. The reaction mixture was cooled and filtered, and the ethanol was evaporated under reduced pressure. The residue was partitioned between diethyl ether and saturated brine. The ether was evaporated and the crude product was distilled in vacuo to give the di-ester, diethyl 3-benzylcyclobutane-1,1-dicarboxylate, b.p. 140°–148° C./0.5mm.Hg.

A mixture of the di-ester (40g.) and potassium heated under reflux overnight. The ethanol was evaporated under reduced pressure, and water (100ml.) was added to the residue. The resulting aqueous solution was washed with diethyl ether (2 × 30ml.), acidified to pH 1 with concentrated hydrochloric acid, and the oily product was extracted into ethyl acetate. The ethyl acetate solution was dried with sodium sulphate and filtered, and the solvent was evaporated under reduced pressure. Pyrolysis of the residue at 180° C. for 30 minutes at 10 mm.Hg. pressure gave 3-benzylcyclobutanecarboxylic acid. This acid was esterified with ethanol, using the process described in the second part of Example 1, to give a mixture of cis and trans isomers of ethyl 3-benzylcyclobutanecarboxylate, b.p. 120°–122° C./1mm.Hg. The n.m.r. spectrum in deuterichloroform showed the following characteristic features (δ values):-

7.10, } 3H, singlets, aromatic protons
7.16, }

4.10, 2H, quartet, —OC$\underline{H}_2$CH$_3$ 2.95, 2H, doublet, PhCH$_2$—<><

1.20, 3H, triplet, -OCH$_2$C$\underline{H}_3$

This ester was converted by the process described in the latter part of Example 1 into a mixture of the cis and trans isomers of the bis(tetrahydropyranyl ether), 15-(3-benzylcyclobutyl)-9α-benzyl-11α,15-bis(tetrahydfropyran-2-yloxy)-16,17,18,19,20-pentanor-5-cis,13-trans-prostadienoic acid.

A solution of the bis(tetrahydropyranyl ether) (291mg.) in acetone (10ml.) was stirred at 0° C. with 8N aqueous chromic acid (0.30ml.) for 10 minutes in an argon atmosphere. Isopropanol (0.10ml.) was then added and stirring was continued for 5 minutes. The reaction mixture was partitioned between ethyl acetate (3 × 15ml.) and saturated aqueous brine (10ml.). The ethyl acetate solution was dried with sodium sulphate and evaporated under reduced pressure. The residue was purified by preparative layer chromatography on silica gel to give the required 9-oxo-bis(tetrahydropyranyl)ether starting material.

EXAMPLE 16

|  | % w/v |
|---|---|
| 9α,11α,15-Trihydroxy-15-(trans-3-phenylcyclobutyl)-16,17,18,19,20-pentanor-5-cis,13-trans-prostadienoic acid. | 0.003 |
| Sodium phosphate B.P. | 2.90 |
| Sodium acid phosphate B.P. | 0.30 |
| Water for injection | to 100 |

The sodium phosphate B.P. was dissolved in about 80% of the water followed by the prostadienoic acid derivative, and when dissolved, the sodium acid phosphate B.P. The solution was made up to volume with water for injection, and the pH was checked to be between 6.7 and 7.7. The solution was filtered to remove particulate matter, sterilised by filtration, and filled into pre-sterilised neutral glass ampoules under aseptic conditions. Immediately before use, the contents of an ampoule are diluted in sodium chloride B.P. for administration by intravenous infusion.

The prostadienoic acid derivative may, of course, be replaced by an equivalent amount of another prostanoic acid derivative of the invention.

EXAMPLE 17

The process described in Example 16 was repeated, omitting the sodium phosphate B.P. and sodium acid phosphate B.P., to give ampoules containing a sterile aqueous solution of 9α,11α,15-trihydroxy-15-(trans-3-phenylcylcobutyl)-16,17,18,19,20-pentanor-5-cis, 13-trans-prostadienoic acid, which are used in the manner described in Example 16.

The prostadienoic acid derivative may be replaced by an equivalent amount of another prostadienoic acid of the invention, to give other sterile aqueous solutions.

What we claim is:-

1. A prostane derivative of the formula:-

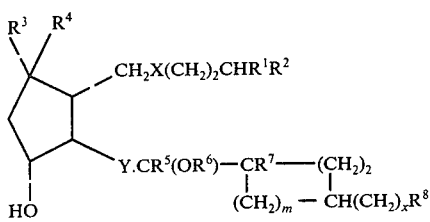

wherein $R^1$ is carboxy or $C_{2-5}$ alkoxycarbonyl, $R^2$, $R^5$ and $R^6$ are each hydrogen, $R^3$ is hydroxy and $R^4$ is hydrogen, X is ethylene or cis-vinylene, Y is ethylene or trans-vinylene, $R^7$ is hydrogen or $C_{1-4}$ alkyl, $R^8$ is phenyl or naphthyl which is unsubstituted or is substituted by halogen, nitro, phenyl, or $C_{1-4}$ alkyl, halogenoalkyl or alkoxy, m and n, which may be the same or different, are each 1 or 2, and x is 0 or 1, and for those compounds wherein $R^1$ is carboxy, the pharmaceutically or veterinarily acceptable salts thereof.

2. The prostane derivative of claim 1 wherein $R^1$ is carboxy, methoxycarbonyl, ethoxycarbonyl or butoxycarbonyl, $R^7$ is hydrogen or methyl and $R^8$ is phenyl or naphthyl which is unsubstituted or bears one substituent selected froom chlorine, fluorine, bromine, nitro, phenyl, methyl, ethyl, propyl, butyl, trifluoromethyl, methoxy, ethoxy, propoxy and butoxy, and $R^2$, $R^3$, $R^4$, $R^5$, $R^6$, X, Y, m, n and x have the meanings stated in claim 1, and for those compounds wherein $R^1$ is carboxy, the ammonium, alkylammonium containing 1 to 4 $C_{1-4}$ alkyls, alkanolammonium containing 1 to 3 2-hydroxyethyls, and alkali metal salts thereof.

3. The prostane derivative of claim 2 wherein $R^1$ is carboxy or methoxycarbonyl, $R^8$ is phenyl or naphthyl which is unsubstituted or bears one substituent selected from chlorine, fluorine, nitro, phenyl, methyl, trifluoromethyl and methoxy, and $R^2$, $R^3$, $R^4$, $R^5$, $R^6$, $R^7$, X, Y, m, n and x have the meanings stated in claim 2.

4. The prostane derivative of claim 2 wherein $R^1$ is carboxy, which is an ammonium, triethylammonium, ethanolammonium, diethanolammonium, sodium or potassium salt.

5. The prostane derivative of claim 1 wherein $R^1$ is carboxy or methoxycarbonyl, $R^2$, $R^5$ and $R^6$ are each hydrogen, X is cis-vinylene, Y is trans-vinylene, $R^7$ is hydrogen or methyl, m and n are each 1, x is 0, and $R^8$ is phenyl, which is unsubstituted or substituted by one chlorine, fluorine, methyl or trifluoromethyl, or unsubstituted naphthyl.

6. The prostane derivative of claim 5 wherein $R^8$ is phenyl, 3-trifluoromethylphenyl, 3-tolyl, 4-fluorophenyl, 4-chlorophenyl or 1-naphthyl.

7. 9α,11α,15α-Trihydroxy-15-(trans-3-phenylcyclobutyl)-16,17,18,19,20-pentanor-5-cis, 13-trans-prostadienoic acid.

8. A pharmaceutical or veterinary composition consisting essentially of the prostane derivative of claim 1 together with a pharmaceutically or veterinarily acceptable diluent or carrier.

9. A method of inducing luteolysis in mammals which comprises administering to mammals in need of such treatment a luteolytically effective amount of the prostane derivative of claim 1.

* * * * *